(12) United States Patent
Lee et al.

(10) Patent No.: US 9,279,083 B2
(45) Date of Patent: Mar. 8, 2016

(54) LIQUID CRYSTAL COMPOUND, LIQUID CRYSTAL COMPOSITION, AND LIQUID CRYSTAL DISPLAY DEVICE

(71) Applicant: DAXIN MATERIALS CORP., Taichung (TW)

(72) Inventors: Ching-Tien Lee, Taichung (TW); Wan-Yu Huang, Taichung (TW); Chun-Chih Wang, Taichung (TW)

(73) Assignee: Daxin Materials Corp., Taichung (TW)

( * ) Notice: Subject to any disclaimer, the term of this patent is extended or adjusted under 35 U.S.C. 154(b) by 0 days.

(21) Appl. No.: 14/788,840

(22) Filed: Jul. 1, 2015

(65) Prior Publication Data

US 2016/0002535 A1    Jan. 7, 2016

(30) Foreign Application Priority Data

Jul. 2, 2014 (TW) .............................. 103122837 A

(51) Int. Cl.
| | |
|---|---|
| *C07D 313/00* | (2006.01) |
| *C09K 19/34* | (2006.01) |
| *C07D 493/08* | (2006.01) |

(52) U.S. Cl.
CPC .......... *C09K 19/3402* (2013.01); *C07D 493/08* (2013.01); *C09K 2019/3425* (2013.01)

(58) Field of Classification Search
CPC ................... C09K 19/3402; C09K 2019/3425; C07D 493/08; C07D 313/00
USPC ............... 252/299.01, 299.6, 299.61, 299.62, 252/299.63, 299.66; 428/1.1; 349/182; 540/1; 549/345, 346
See application file for complete search history.

(56) References Cited

U.S. PATENT DOCUMENTS 5,466,710 A * 11/1995 Weston ................. A01N 43/90 514/452
6,808,762 B2 * 10/2004 Bremer ................ C07D 493/08 252/299.61

\* cited by examiner

*Primary Examiner* — Geraldina Visconti
(74) *Attorney, Agent, or Firm* — The Mueller Law Office, P.C.

(57) ABSTRACT

A liquid crystal compound of formula (I):

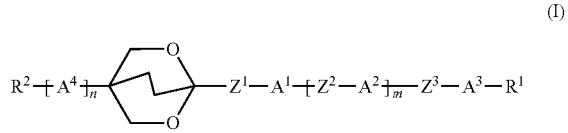

(I)

where $A^1$, $A^2$, $A^3$, $A^4$, $R^1$, $R^2$, $Z^1$, $Z^2$, $Z^3$, n, and m are as defined in the specification.

11 Claims, No Drawings

LIQUID CRYSTAL COMPOUND, LIQUID CRYSTAL COMPOSITION, AND LIQUID CRYSTAL DISPLAY DEVICE

CROSS-REFERENCE TO RELATED APPLICATION

This application claims the priority of Taiwan application no. 103122837, filed on Jul. 2, 2014, the disclosure of which is incorporated in its entirety herein by reference.

FIELD

The disclosure relates to a liquid crystal compound having a dioxabicyclo[2.2.2]octane ring moiety, a liquid crystal composition including the liquid crystal compound, and a liquid crystal display device including the liquid crystal compound.

BACKGROUND

There are various operation modes of the liquid crystal devices, such as a phase change (PC) mode, a twisted nematic (TN) mode, a super twisted nematic (STN) mode, a bistable twisted nematic (BTN) mode, an electrically controlled birefringence (ECB) mode, an optically compensated bend (OCB) mode, a fringe field switching (FFS) mode, an in-plane switching (IPS) mode, a vertical alignment (VA) mode, and a polymer sustained alignment (PSA) mode. A liquid crystal composition includes liquid crystal compounds, and may require the following characteristics: (1) chemical stability and physical stability; (2) a suitable refractive index anisotropy ($\Delta n$); (3) a suitable dielectric anisotropy ($\Delta \epsilon$); (4) a high clearing point ($T_{ni}$, nematic-to-liquid transition temperature); (5) a low minimum temperature of the nematic phase; and (6) an excellent compatibility with other liquid crystal compounds.

U.S. Pat. No. 6,808,762 B2 discloses a liquid crystal compound having an oxabicyclooctane ring moiety. US patent application publication no. 2014/0021407 A1 discloses a liquid crystal compound having a 2,6,7-trioxabicyclo[2.2.2]octane ring moiety. To the knowledge of the inventors, a liquid crystal compound having a dioxabicyclo[2.2.2]octane ring moiety, intermediate products of the liquid crystal compound, and processes to synthesize the liquid crystal compounds have not been disclosed.

SUMMARY

Embodiments of the disclosure attempt to provide a liquid crystal compound having a dioxabicyclo[2.2.2]octane ring moiety. The liquid crystal compound has a high dielectric anisotropy, a low rotational viscosity ($\gamma_1$), a suitable refractive index anisotropy ($\Delta n$), a wide temperature range of the nematic phase, good compatibility with known liquid crystal compounds, good stability to heat and light, etc.

A first embodiment of the disclosure attempts to provide a liquid crystal compound of formula (I):

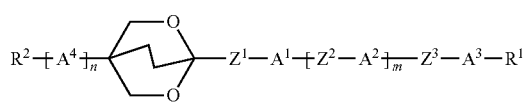

where:
$A^1$, $A^2$, $A^3$, and $A^4$ are each independently 1,4-cyclohexylene or halogen-substituted or unsubstituted 1,4-phenylene;
$R^1$ is a halogen atom, —CN, a halogen-substituted or unsubstituted C1-C10 alkyl group, a halogen-substituted or unsubstituted C2-C10 alkenyl group, a halogen-substituted or unsubstituted C2-C10 alkynyl group, a halogen-substituted or unsubstituted C1-C10 alkoxyl group, a halogen-substituted or unsubstituted C1-C10 alkylthio group, or a halogen-substituted or unsubstituted C2-C10 alkenyloxy group;
$R^2$ is a hydrogen atom, a C1-C10 alkyl group, or a C1-C10 halogen-substituted alkyl group;
$Z^1$, $Z^2$, and $Z^3$ are each independently a single bond, —COO—, —OCO—, —CF$_2$O—, —OCF$_2$—, —C≡C—, or —CH=CH—; and
n and m are each independently 0 or 1.

A second embodiment of the disclosure attempts to provide a liquid crystal composition which includes the liquid crystal compound of formula (I).

A third embodiment of the disclosure attempts to provide a liquid crystal display device which includes the liquid crystal compound of formula (I).

DETAILED DESCRIPTION

A liquid crystal compound according to a first embodiment of the present disclosure is represented by formula (I):

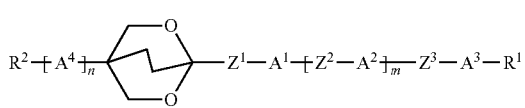

where:
$A^1$, $A^2$, $A^3$, and $A^4$ are each independently 1,4-cyclohexylene or halogen-substituted or unsubstituted 1,4-phenylene;
$R^1$ is a halogen atom, —CN, a halogen-substituted or unsubstituted C1-C10 alkyl group, a halogen-substituted or unsubstituted C2-C10 alkenyl group, a halogen-substituted or unsubstituted C2-C10 alkynyl group, a halogen-substituted or unsubstituted C1-C10 alkoxyl group, a halogen-substituted or unsubstituted C1-C10 alkylthio group, or a halogen-substituted or unsubstituted C2-C10 alkenyloxy group;
$R^2$ is a hydrogen atom, a C1-C10 alkyl group, or a halogen-substituted C1-C10 alkyl group;
$Z^1$, $Z^2$, and $Z^3$ are each independently a single bond, —COO—, —OCO—, —CF$_2$O—, —OCF$_2$—, —C≡C—, or —CH=CH—; and
n and m are each independently 0 or 1.

Preferably, $A^1$, $A^2$, and $A^3$ are each independently halogen-substituted or unsubstituted 1,4-phenylene, and n is 0. More preferably, $A^1$, $A^2$, and $A^3$ are each independently 1,4-phenylene, 2-fluoro-1,4-phenylene, 3-fluoro-1,4-phenylene, 2,3-difluoro-1,4-phenylene, or 3,5-difluoro-1,4-phenylene.

Hereinafter, the liquid crystal compound of formula (I) is referred to as liquid crystal compound (I).

Preferably, $R^1$ is a halogen atom, —CN, —CF$_3$, —OCF$_3$, —OCH=CF$_2$, —OCF$_2$CF=CF$_2$, a C1-C10 alkyl group or a C1-C10 alkoxyl group.

Preferably, $R^2$ is a hydrogen atom, a C1-C5 alkyl group, or a halogen-substituted C1-C5 alkyl group.

Preferably, $Z^1$, $Z^2$, and $Z^3$ are each independently a single bond or —CF$_2$O—.

More preferably, $A^1$, $A^2$, and $A^3$ are each independently 1,4-phenylene, 2-fluoro-1,4-phenylene, 3-fluoro-1,4-phenylene, 2,3-difluoro-1,4-phenylene, or 3,5-difluoro-1,4-phenylene; $Z^1$, $Z^2$, and $Z^3$ are each independently a single bond or —$CF_2O$—; n=0; and m=0 or 1.

Non-limiting examples of the liquid crystal compound (I) include Compounds (I-1) to (I-6), which are represented by the following formulas:

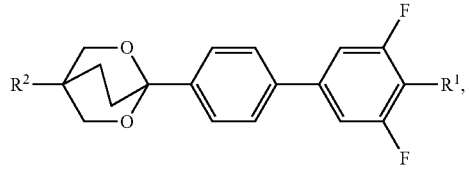
(I-1)

(I-2)

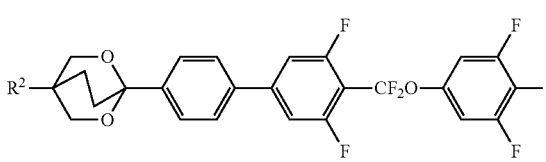
(I-3)

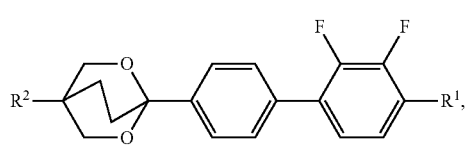
(I-4)

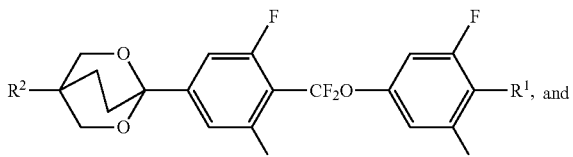
(I-5)

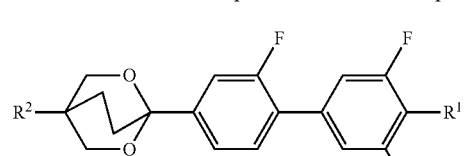
(I-6)

where $R^1$ and $R^2$ are as defined aforementioned.

Specific examples of the liquid crystal compound (I) include Compounds (I-1-1), (I-1-2), (I-1-3), (I-1-4), (I-1-5), (I-1-6), (I-2-1), (I-2-2), (I-2-3), (I-3-1), (I-3-2), (I-3-3), (I-3-4), (I-3-5), (I-4-1), (I-5-1), and (I-6-1), which are respectively represented by the following formulas:

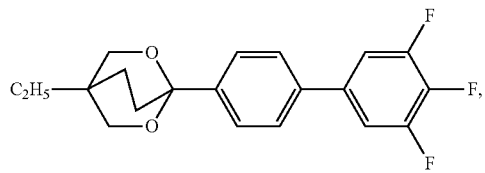
(I-1-1)

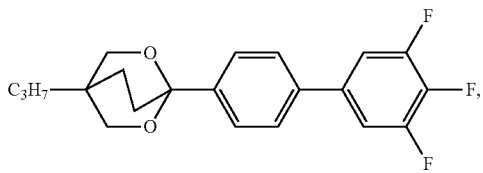
(I-1-2)

(I-1-3)

(I-1-4)

(I-1-5)

(I-1-6)

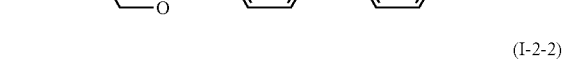
(I-2-1)

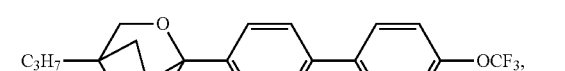
(I-2-2)

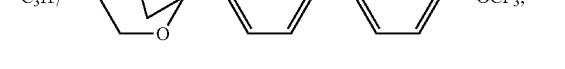
(I-2-3)

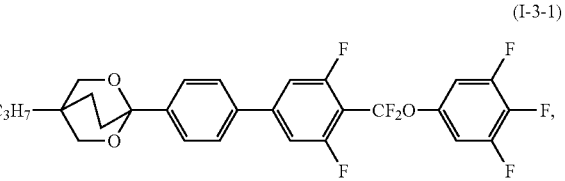
(I-3-1)

(I-3-2)
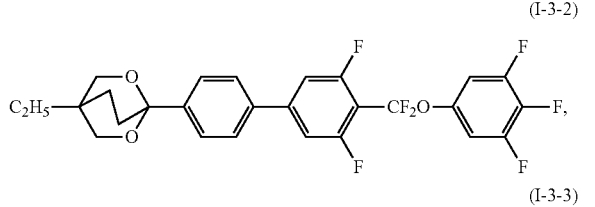
(I-3-3)
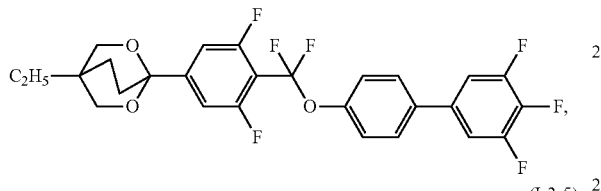
(I-3-4)
(I-3-5)
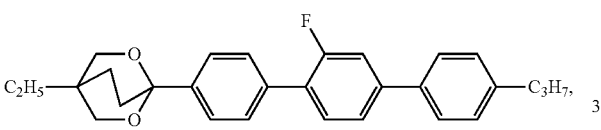
(I-4-1)
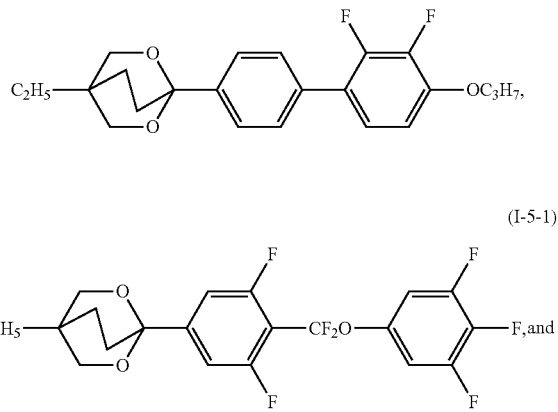
(I-5-1)
(I-6-1)
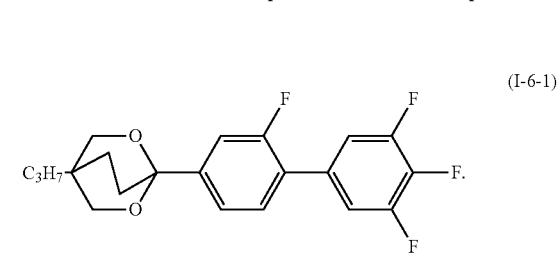
In this embodiment, the liquid crystal compound (I) is prepared from the precursor of formula (I'-2) which can be made by the synthetic steps depicted in Scheme 1.
Scheme I
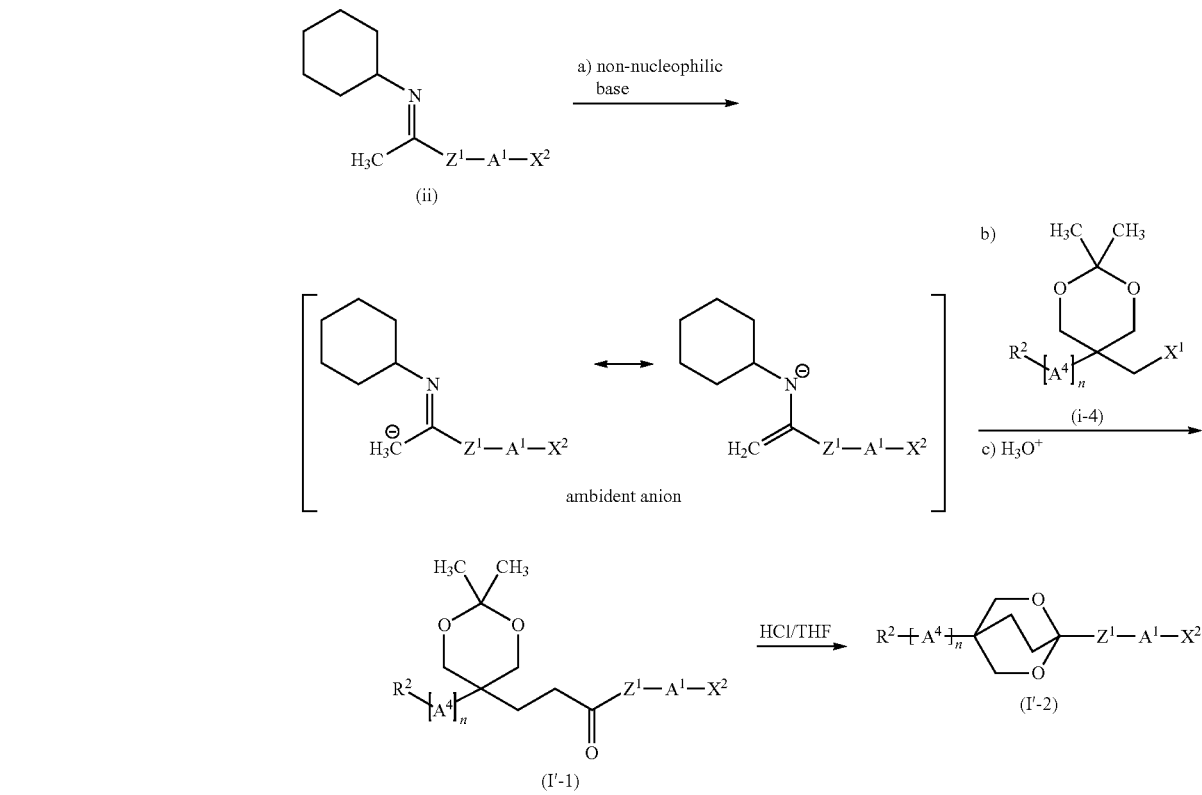

where $A^1$, $A^4$, $Z^1$, $R^2$, and n are as defined aforementioned, $X^1$ is a halogen atom, and $X^2$ is a halogen atom or a hydrogen atom.

An imine compound of formula (ii) is deprotonated with a non-nucleophilic base such as lithium diisopropylamide (LDA), lithium tetramethylpiperidide (LIMP), lithium bis(trimethylsily)amide (LHMDS), sodium bis(trimethylsilyl)amide (NaHMDS), and potassium bis(trimethylsilyl)amide (KHMDS), followed by substitution reaction with acetonide compound of formula (i-4) to give (I'-1). Under acidic condition, (I'-1) can be converted to (I'-2) through deprotection and intramolecular cyclization consecutively.

The 1,3-dioxane compound of formula (i-4) can be synthesized as depicted in Scheme II:

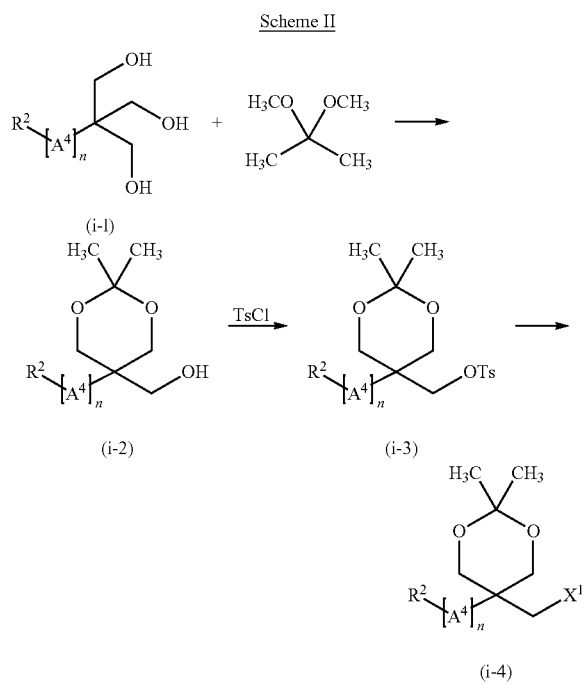

where $A^4$, $R^2$, n, and $X^1$ are as defined aforementioned. The steps for synthesizing acetonide compound of formula (i-4) will be described in Synthesis Example 1 hereinafter.

The liquid crystal compound (I) can be synthesized from the intermediate of formula (I'-2) by using one of the following three approaches A, B and C.

In the approach A, the formula (I'-2) is coupled with an organometallic reagent in the presence of a palladium(0), as shown in Scheme III:

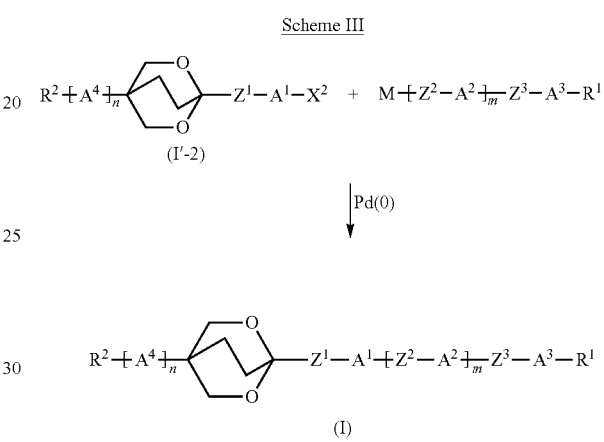

where $A^1$, $A^2$, $A^3$, $A^4$, $R^1$, $R^2$, $Z^1$, $Z^3$, n, m, and $X^2$ are as defined above, $Z^2$ is a single bond, —C≡C—, or —CH=CH—, and M is —B(OR)$_2$, —SnR$_3$, —ZnY, —MgY in which R is a hydrogen atom or an alkyl group and Y is a halogen atom.

The approach B is represented by Scheme IV:

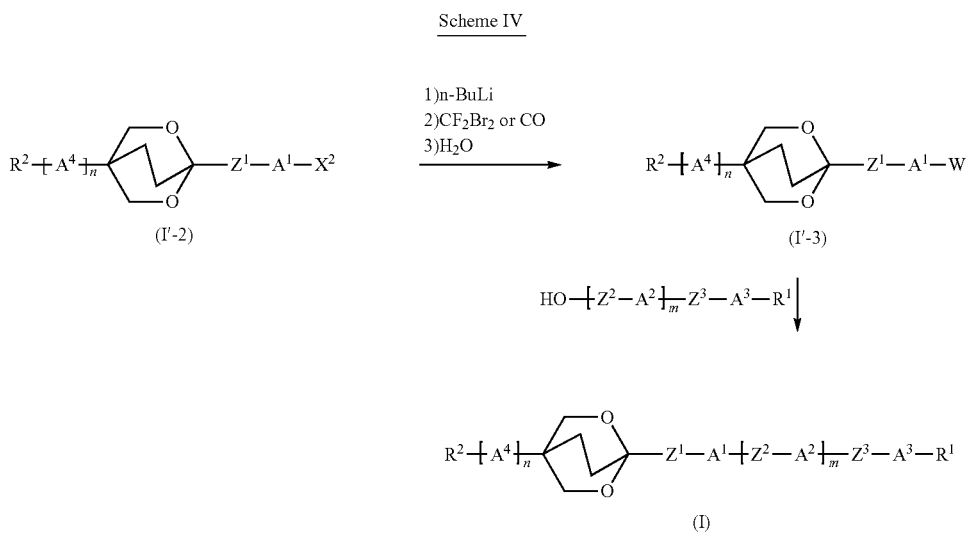

where $A^1$, $A^2$, $A^3$, $A^4$, $R^{1,}$ $R^2$, $Z^1$, $Z^3$, n, m, and $X^2$ are as defined aforementioned, $Z^2$ is —COO— or —$CF_2O$—, and W is $CF_2Br$ or COOH.

In the approach B, the formula (I'-2) is deprotonated with an organolithium reagent (n-BuLi), and then reacted with $CF_2Br_2$ or $CO_2$ in an addition reaction to obtain a compound of formula (I'-3). The formula (I'-3) is reacted with an alcohol reagent represented by

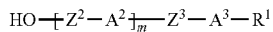

in a substitution reaction to obtain the liquid crystal compound of formula (I).

The approach C is represented by Scheme V:

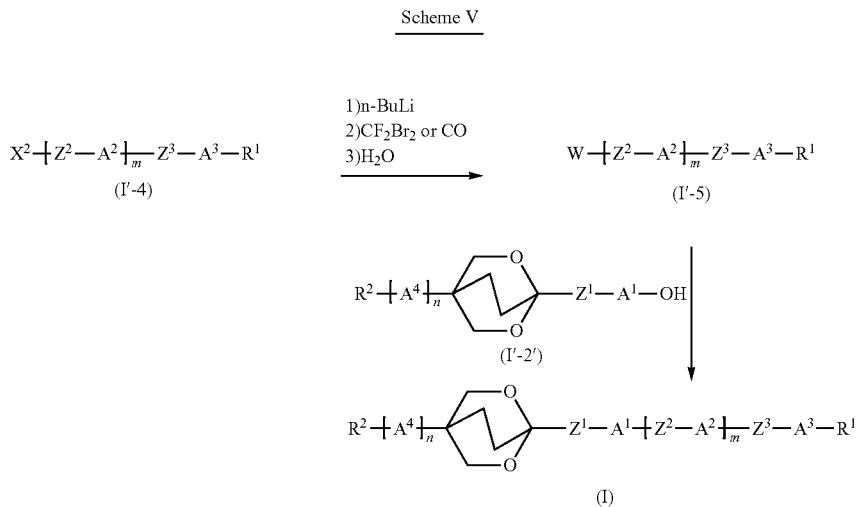

where $A^1$, $A^2$, $A^3$, $A^4$, $R^{1,}$ $R^2$, $Z^1$, $Z^3$, n, m, $X^2$, and W are as defined aforementioned, and $Z^2$ is —OCO— or —$OCF_2$—. The formula (I'-2') is prepared from the second intermediate product of formula (I'-2).

In the approach C, the formula (I'-4) is reacted with an organolithium reagent (n-BuLi), and then reacted with $CF_2Br_2$ or $CO_2$ in an addition reaction to obtain a compound of formula (I'-5). The formula (I'-5) is reacted with the formula (I'-2') in a substitution reaction to obtain the liquid crystal compound of formula (I).

A liquid crystal composition according to a second embodiment of the present disclosure includes the liquid crystal compound (I) and a liquid crystal compound of formula (II):

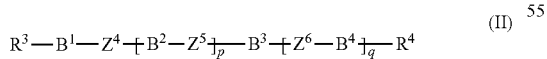

where:
$B^1$, $B^2$, $B^3$, and $B^4$ are each independently 1,4-cyclohexylene, halogen-substituted or unsubstituted 1,4-phenylene, or 2,5-indanylene;

$R^3$ is a halogen atom, a halogen-substituted or unsubstituted C1-C10 alkyl group, a halogen-substituted or unsubstituted C2-C10 alkenyl group, a halogen-substituted or unsubstituted C2-C10 alkynyl group, or a halogen-substituted or unsubstituted C1-C10 alkoxyl group;

$R^4$ is a halogen atom, —CN, a halogen-substituted or unsubstituted C1-C10 alkyl group, a halogen-substituted or unsubstituted C2-C10 alkenyl group, or a halogen-substituted or unsubstituted C1-C10 alkoxyl group;

$Z^4$, $Z^5$, and $Z^6$ are each independently a single bond, —$(CH_2)_2$—, —COO—, —OCO—, —$CF_2O$—, —$OCF_2$—, —C≡C—, or —CH═CH—; and p and q are each independently 0 or 1.

Hereinafter, the liquid crystal compound of formula (II) is referred to as liquid crystal compound (II).

Preferably, $R^3$ is a C1-C10 alkyl group, and $R^4$ is a halogen atom, —CN, a C1-C10 alkyl group, a C2-C10 alkenyl group, —$CF_3$, or —$OCF_3$.

Non-limiting examples of the liquid crystal compound (II) include Compounds (II-1) to (II-22), which are respectively represented by the following formulas:

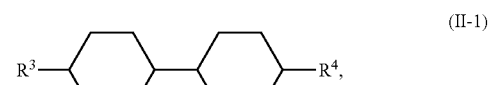

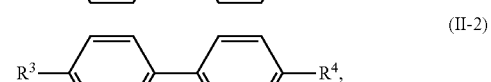

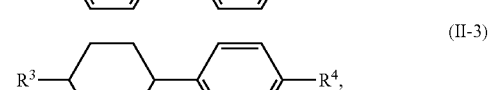

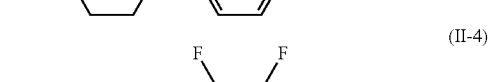

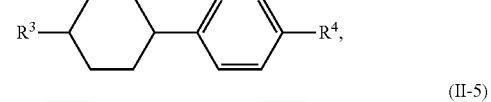

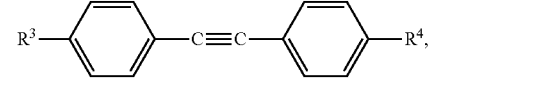

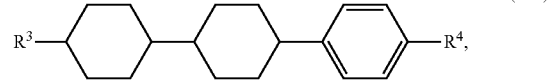

(II-7) 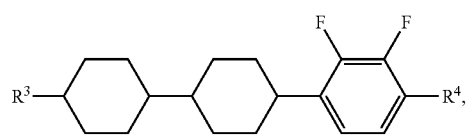

(II-8) 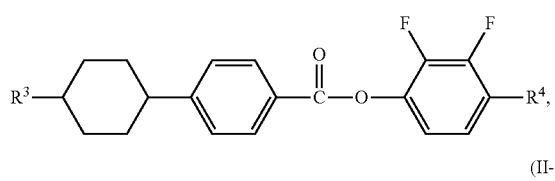

(II-9) 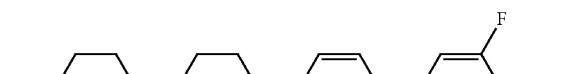

(II-10) 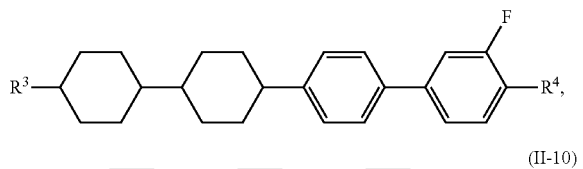

(II-11) 

(II-12) 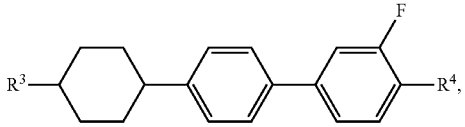

(II-13) 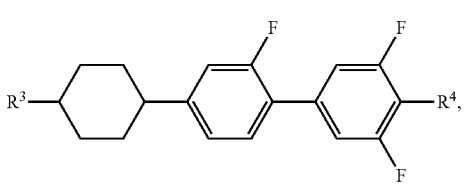

(II-14) 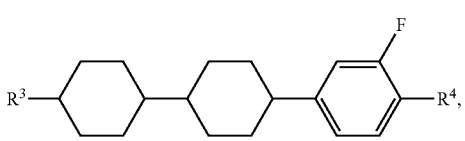

(II-15) 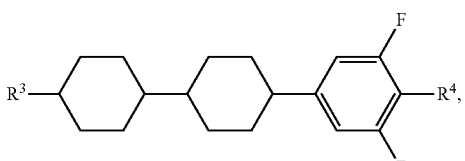

(II-16) 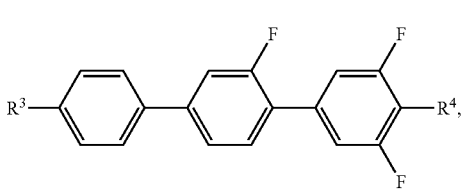

(II-17) 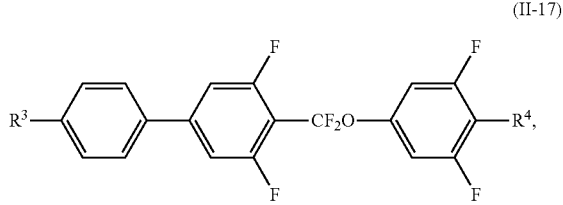

(II-18) 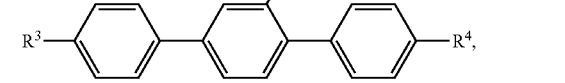

(II-19) 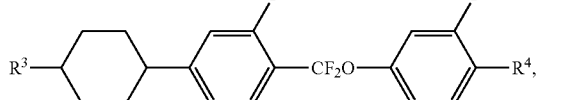

(II-20) 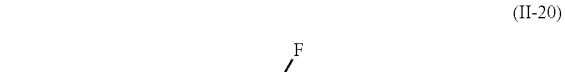

(II-21) 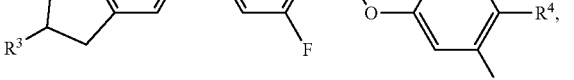

(II-22) 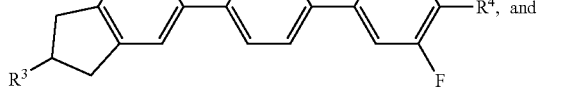

where $R^3$ is hydrogen, a C1-C5 alkyl group, or a C2-C5 alkenyl group, and $R^4$ is fluorine, —CN, a C1-C5 alkyl group, a C2-C5 alkenyl group, methoxy, ethoxy, —OCHCF$_2$ or —OCF$_3$. In non-limiting examples of the liquid crystal compound of formula (II), $R^3$ is hydrogen, methyl, ethyl, propyl, butyl, pentyl, 3-butenyl(—CH$_2$—CH$_2$—CH=CH$_2$), or vinyl, and $R^4$ is fluorine, —CN, vinyl, 1-propenyl (—CH=CH—CH$_3$), methyl, ethyl, propyl, butyl, methoxy, ethoxy, —OCHCF$_2$ or —OCF$_3$.

Specific examples of compounds (II-1) to (II-22) include compounds listed in Table 1.

TABLE 1

| Compound | Compound | $R^3$ | $R^4$ |
|---|---|---|---|
| II-1 | II-1-1 | propyl | vinyl |
|  | II-1-2 | propyl | 1-propenyl |

TABLE 1-continued

| Compound | Compound | R³ | R⁴ |
|---|---|---|---|
|  | II-1-3 | propyl | pentyl |
|  | II-1-4 | propyl | methoxy |
| II-2 | II-2-1 | pentyl | methyl |
| II-3 | II-3-1 | pentyl | propyl |
|  | II-3-2 | propyl | —CN |
|  | II-3-3 | pentyl | —CN |
| II-4 | II-4-1 | propyl | methoxy |
| II-5 | II-5-1 | methyl | ethoxy |
|  | II-5-2 | propyl | fluorine |
|  | II-5-3 | 3-butenyl | 3-butenyl |
| II-6 | II-6-1 | propyl | methyl |
|  | II-6-2 | propyl | fluorine |
|  | II-6-3 | propyl | —OCF₃ |
|  | II-6-4 | pentyl | —OCF₃ |
| II-7 | II-7-1 | propyl | methyl |
|  | II-7-2 | propyl | methoxy |
| II-8 | II-8-1 | propyl | ethoxy |
| II-9 | II-9-1 | propyl | fluorine |
| II-10 | II-10-1 | propyl | ethyl |
|  | II-10-2 | propyl | fluorine |
|  | II-10-3 | pentyl | —CN |
| II-11 | II-11-1 | propyl | fluorine |
| II-12 | II-12-1 | propyl | fluorine |
| II-13 | II-13-1 | ethyl | fluorine |
|  | II-13-2 | propyl | fluorine |
|  | II-13-3 | pentyl | fluorine |
|  | II-13-4 | vinyl | fluorine |
|  | II-13-5 | ethyl | —OCF₃ |
|  | II-13-6 | propyl | —OCF₃ |
| II-14 | II-14-1 | propyl | fluorine |
| II-15 | II-15-1 | propyl | fluorine |
| II-16 | II-16-1 | propyl | ethyl |
|  | II-16-2 | propyl | ethoxy |
| II-17 | II-17-1 | propyl | fluorine |
| II-18 | II-18-1 | propyl | ethyl |
| II-19 | II-19-1 | propyl | fluorine |
| II-20 | II-20-1 | propyl | —OCF₃ |
| II-21 | II-21-1 | ethyl | —OCHCF₂ |
| II-22 | II-22-1 | hydrogen | fluorine |
|  | II-22-2 | methyl | fluorine |
|  | II-22-3 | ethyl | fluorine |

In the liquid crystal composition, the amounts of the liquid crystal compound (I) and the liquid crystal compound (II) can be adjusted based on requirements. In this embodiment, based on the total weight of the liquid crystal composition, the amount of the liquid crystal compound (I) preferably ranges from 2 wt % to 50 wt %, more preferably from 2 wt % to 30 wt %. Based on the total weight of the liquid crystal composition, the amount of the liquid crystal compound (II) preferably ranges from 30 wt % to 98 wt %, more preferably from 50 wt % to 98 wt %.

A liquid crystal display device according to a third embodiment of the present disclosure includes the liquid crystal compound (I).

The embodiments of the disclosure will now be explained in more detail below.

Synthesis Example 1

5-ethyl-5-iodomethyl-2,2-dimethyl-[1,3]dioxane (Compound i-4-1) was synthesized by steps (a-1) to (a-3) as depicted in Scheme 1:

Scheme 1

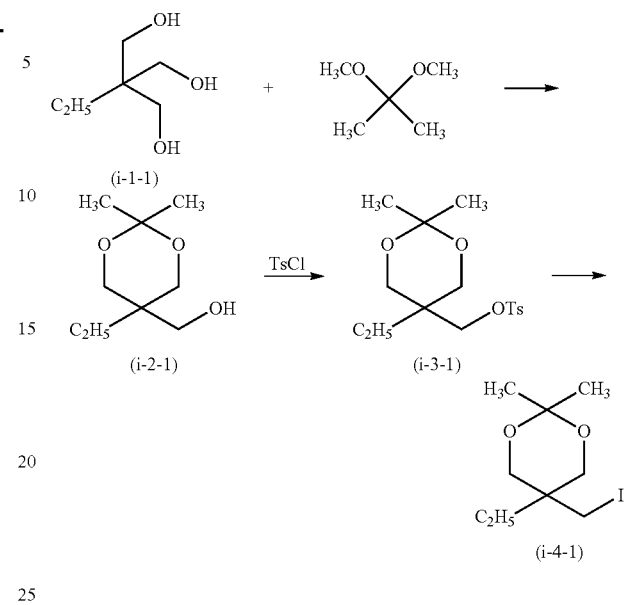

Step (a-1)—Synthesis of (5-ethyl-2,2-dimethyl-[1,3]dioxan-5-yl)-methanol (Compound (i-2-1) in Scheme 1):

To a 250 ml two-neck round-bottom flask, 100 ml of dichloromethane ($CH_2Cl_2$), 2-hydroxymethyl-2-ethyl-propane-1,3-diol (i.e., Compound (i-1-1) in Scheme 1) (13.4 g, 0.1 mol), 2,2-dimethoxypropane (9.2 g, 0.15 mol), and 4-methylbenzenesulfonic acid (0.1 g) were sequentially added to obtain a mixture. The mixture was stirred at room temperature for 18 hours. A thin-layer chromatography (TLC) plate (solvent: ethyl acetate) was used to check if the reaction was completed. After the reaction was completed, 100 ml of deionized water was added to the two-neck round-bottom flask to quench the reaction. The contents in the two-neck round-bottom flask were extracted three times with dichloromethane and an organic layer was collected. The organic layer was dried with magnesium sulfate anhydrous, followed by filtration and condensation under a reduced pressure to obtain a yellow liquid (17.8 g), which was Compound (i-2-1).

Step (a-2)—Synthesis of toluene-4-sulfonic acid 5-ethyl-2,2-dimethyl-[1,3]dioxan-5-ylmethyl ester (Compound (i-3-1) in Scheme 1):

To a 250 ml two-neck round-bottom flask, 20 ml of dichloromethane, Compound (i-2-1) (10.0 g, 0.058 mol), 5.5 ml of pyridine, and 4-toluenesulfonyl chloride (10.1 g, 0.053 mol) were sequentially added to obtain a mixture. The mixture was stirred at room temperature for 18 hours. A thin-layer chromatography (TLC) plate (volume ratio of ethyl acetate:n-hexane=3:7) was used to check if the reaction was completed. After the reaction was completed, 100 ml of deionized water was added to the two-neck round-bottom flask to quench the reaction. The contents in the two-neck round-bottom flask were extracted three times with dichloromethane and an organic layer was collected. The organic layer was dried with magnesium sulfate anhydrous and was filtered to collect a filtrate. The filtrate was condensed under a reduced pressure, followed by column chromatography (volume ratio of ethyl acetate:n-hexane=3:7) to obtain white solids (14.3 g), which were Compound (i-3-1).

Step (a-3)—Synthesis of Compound (i-4-1):

To a 250 ml two-neck round-bottom flask, 20 ml of acetone, Compound (i-3-1) (3.3 g, 0.01 mol), and sodium iodide (3.75 g, 0.025 mol) were sequentially added to obtain a mixture. The mixture was stirred at room temperature for 18 hours. A thin-layer chromatography (TLC) plate (volume ratio of ethyl acetate:n-hexane=1:9) was used to check if the reaction was completed. After the reaction was completed, 100 ml of deionized water was added to the two-neck round-bottom flask to quench the reaction. The contents in the two-neck round-bottom flask were extracted three times with dichloromethane and organic layer was collected. The organic layer was dried with magnesium sulfate anhydrous and was filtered to collect a filtrate. The filtrate was condensed under a reduced pressure, followed by column chromatography (volume ratio of ethyl acetate:n-hexane=1:9) to obtain a light yellow liquid (1.9 g), which was Compound (i-4-1).

Synthesis Example 2

(1-(4-Bromo-phenyl)-ethylidene)-cyclohexyl-amine (Compound ii-1) was synthesized as depicted in Scheme 2:

Scheme 2

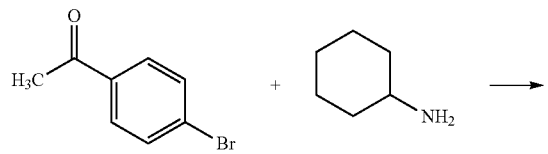

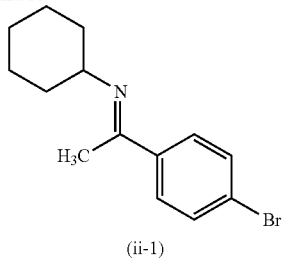

(ii-1)

To a 250 ml two-neck round-bottom flask, 40 ml of toluene, p-bromoacetophenone (4 g, 0.02 mol), cyclohexylamine (3 g, 0.03 mol), 4-methylbenzenesulfonic acid (0.04 g), and 2 g of molecular sieve were sequentially added to obtain a mixture. The mixture was heated under reflux for 18 hours, and then filtered through a short pad of celite. The filtrate was collected and then condensed under a reduced pressure to obtain yellow solids (4.8 g), which were Compound (ii-1).

Example 1

Synthesis of a liquid crystal compound (Compound I-1-1) of formula (I-1-1) is shown in the following Scheme 3:

Compound I-1-1 was synthesized by steps (b-1) to (b-3) according to Scheme 3:

Scheme 3

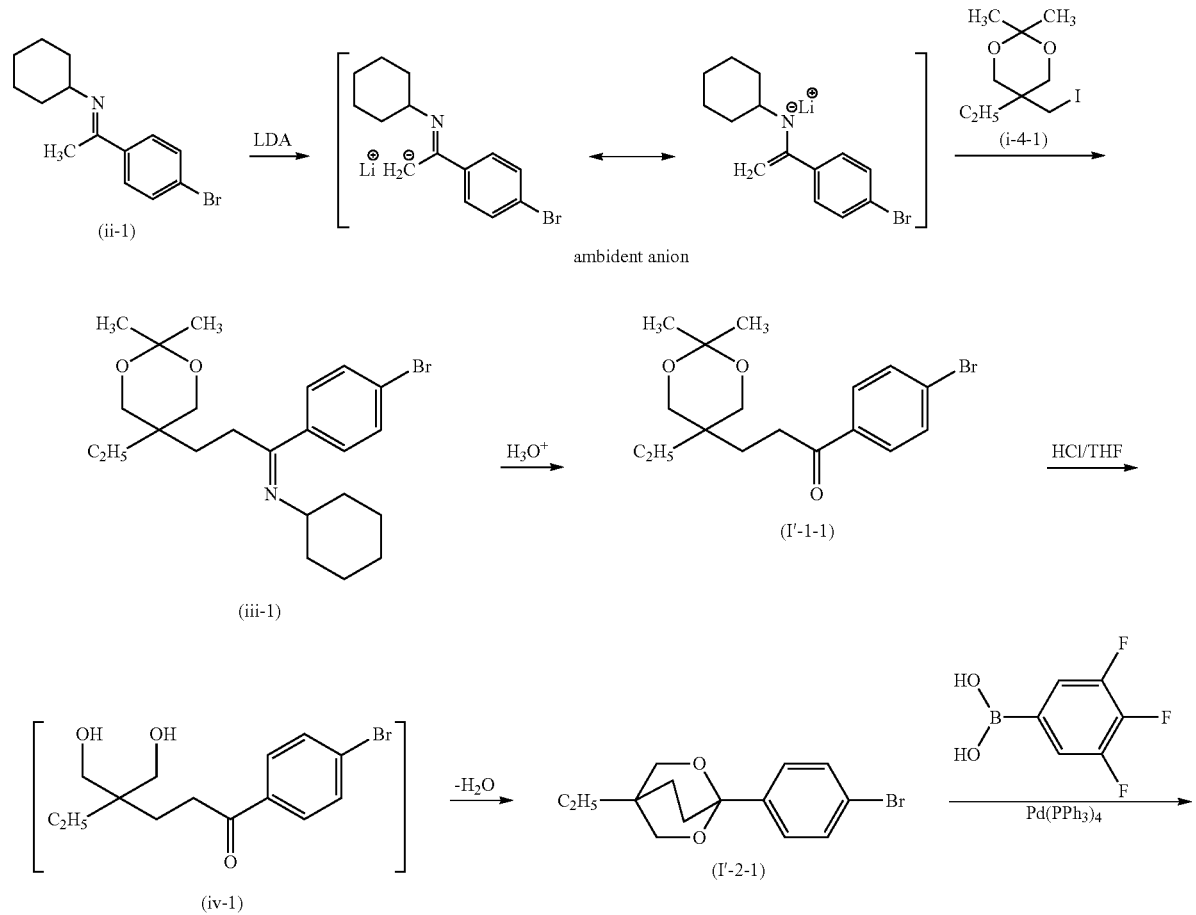

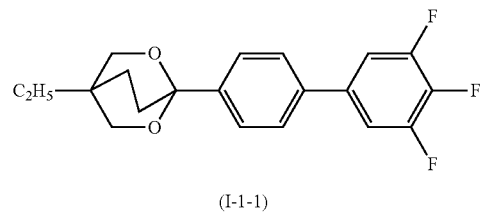

(I-1-1)

Step (b-1)—Synthesis of 1-(4-bromo-phenyl)-3-(5-ethyl-2,2-dimethyl-[1,3]dioxan-5-yl)-propan-1-one (Compound I'-1-1 in Scheme 3):

To a 250 ml two-neck round-bottom flask, 45 ml of tetrahydrofuran (THF) and 6.4 ml of diisopropylamine were sequentially added under nitrogen atmosphere. Then, the contents in the flask were cooled to 0° C., 16 ml of n-butyllithium solution (2.5 M) was slowly added to the flask, followed by stirring at 0° C. for 30 minutes to obtain lithium diisopropylamide (LDA) in THF. Next, Compound (ii-1) (9 g, 0.032 mol) was added to the flask, followed by stirring for 1 hour. The THF solution of Compound i-4-1 (8.5 g, 0.03 mol) was then introduced into the flask and the temperature of the resulting mixture was allowed to warm to room temperature. The resulting mixture was then heated under reflux for 18 hours. A thin-layer chromatography (TLC) plate (volume ratio of ethyl acetate:n-hexane=1:10) was used to check if the reaction was completed. I After the reaction was completed, 50 ml of deionized water was added to the flask to quench the reaction. The contents in the flask were extracted three times with ethyl acetate to collect an organic layer. The organic layer was dried with using magnesium sulfate anhydrous and was filtered to collect a filtrate. The filtrate was condensed under a reduced pressure, followed by column chromatography (volume ratio of ethyl acetate:n-hexane=1:10) to obtain a brown liquid (5.1 g), which was Compound I'-1-1.

Step (b-2)—Synthesis of Compound I'-2-1 in Scheme 3:

To a 250 ml two-neck round-bottom flask, 30 ml of THF, Compound (I'-1-1) (2.9 g, 8 mmol), and 30 ml of an aqueous hydrogen chloride solution (2N) were sequentially added to obtain a mixture. The mixture was stirred at room temperature for 2 hours. A thin-layer chromatography (TLC) plate (volume ratio of ethyl acetate:n-hexane=1:10) was used to check if the reaction was completed. After the reaction was completed, 50 ml of deionized water was added to the flask to quench the reaction. The contents in the flask were extracted three times with ethyl acetate and the organic layer was collected. The organic layer was dried with magnesium sulfate anhydrous and was filtered to collect a filtrate. The filtrate was condensed under a reduced pressure, followed by column chromatography (volume ratio of ethyl acetate:n-hexane=1:10) to obtain light yellow solids (1.9 g), which were Compound I'-2-1.

Step (b-3)—Synthesis of Compound I-1-1 in Scheme 3:

In a 250 ml two-neck round-bottom flask, 15 ml of THF, Compound (I'-2-1) (0.3 g, 0.1 mmol), 3,4,5-trifluorophenylboronic acid (0.26 g, 0.14 mmol), 3 ml of an aqueous potassium carbonate solution (1N), and tetrakis(triphenylphosphane)palladium(0) [Pd(PPh$_3$)$_4$] (0.05 g) were sequentially added to obtain a mixture. The mixture was heated under reflux for 18 hours for reaction. A thin-layer chromatography (TLC) plate (volume ratio of ethyl acetate:n-hexane=1:10) was used to check if the reaction was completed. After the reaction was completed, 50 ml of deionized water was added to the flask to quench the reaction. The contents in the flask were extracted three times with ethyl acetate and the organic layer was collected. The organic layer was dried with magnesium sulfate anhydrous and was filtered to collect a filtrate. The filtrate was condensed under a reduced pressure, followed by column chromatography (volume ratio of ethyl acetate:n-hexane=1:10) to obtain white solids (0.3 g). The spectrum analysis for the white solids is: $^1$H-NMR (CDCl$_3$, 400 MHz), δ (ppm): 0.865 (t, 3H, J=8 Hz), 1.275 (q, 2H, J=8 Hz), 1.823(m, 2H), 2.228 (m, 2H), 4.011 (s, 4H), 7.168(dd, 2H, J=8.8-2.4 Hz), 7.462 (d, 2H, J=8.4 Hz), 7.594 (d, 2H, J=8.4 Hz); GC-MS: m/z=348.3141 [M]$^+$. The white solids were confirmed to be Compound (I-1-1).

Example 2

Synthesis of a liquid crystal compound (Compound I-1-2):

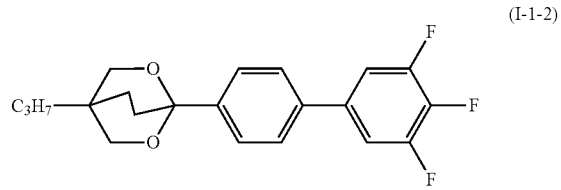

(I-1-2)

Compound I-1-2 was synthesized according to the procedures described in [Synthesis Example 1], [Synthesis Example2], and [Example 1], except that, for synthesizing Compound I-1-2, 2-hydroxymethyl-2-propyl-propane-1,3-diol (0.1 mol) was used to replace Compound i-1-1 used in step (a-1). The spectrum analysis for the compound obtained by the above procedures is: $^1$H-NMR (CDCl$_3$, 400 MHz), δ (ppm): 0.922 (t, 3H, J=8 Hz), 1.144-1.306 (m, 4H), 1.815-1.856 (m, 2H), 2.199-2.252 (m, 2H), 3.995 (s, 4H), 7.165 (dd, 2H, J=8.8-2.4 Hz), 7.460 (d, 2H, J=8.4 Hz), 7.596 (d, 2H, J=8.4 Hz); GC-MS: m/z=362.1838 [M]$^+$. The compound obtained was confirmed to be Compound (I-1-2).

Example 3

Synthesis of a liquid crystal compound (Compound I-2-2):

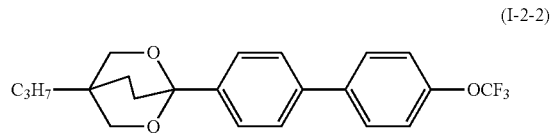

(I-2-2)

Compound I-2-2 was synthesized according to the procedures described in [Synthesis Example 1], [Synthesis Example2], and [Example 1], except that, for synthesizing Compound I-2-2, 2-hydroxymethyl-2-propyl-propane-1,3- diol (0.1 mol) was used to replace Compound i-1-1 used in step (a-1), and 4-(trifluoromethoxy)phenylboronic acid (0.14 mmol) was used to replace 3,4,5-trifluorophenylboronic acid used in step (b-3). The spectrum analysis for the compound obtained by the above procedures is: $^1$H-NMR (CDCl$_3$, 400 MHz), δ (ppm): 0.924 (t, 3H, J=8.4 Hz), 1.115-1.309 (m 4H), 1.818-1.859 (m, 2H), 2.235-2.275 (m, 2H), 3.999 (s, 4H), 7.265 (d, 2H, J=8 Hz), 7.511-7.601 (m, 6H); GC-MS: m/z=392.0558 [M]$^+$. The compound obtained was confirmed to be Compound I-2-2.

Example 4

Synthesis of a liquid crystal compound (Compound I-3-1):

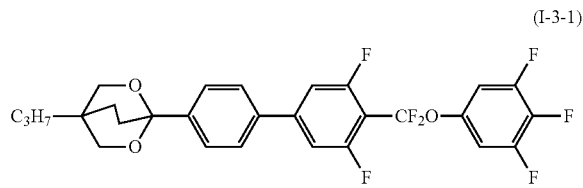

The liquid crystal compound I-3-1 was synthesized according to the procedures described in [Synthesis Example 1], [Synthesis Example 2], and [Example 1], except that, for synthesizing Compound I-3-1, 2-hydroxymethyl-2-propyl-propane-1,3-diol (0.1 mol) was used to replace Compound i-1-1 used in step (a-1), and [4-[difluoro(3,4,5-trifluorophenoxy)methyl]-3,5-difluorophenyl]boronic acid (0.14 mmol) was used to replace 3,4,5-trifluorophenylboronic acid used in step (b-3). The spectrum analysis for the compound obtained by the above procedures is: $^1$H-NMR (CDCl$_3$, 400 MHz), δ (ppm): 0.906 (t, 3H, J=8 Hz), 1.156-1.308 (m, 4H), 1.821-1.861 (m,2H), 2.212-2.252 (m, 2H), 4.000 (s,4H), 6.980 (d, 2H, J=8.4 Hz), 7.205 (d, 2H, J=10.8 Hz), 7.532 (d, 2H, J=8.8 Hz), 7.628 (d, 2H, J=8.4 Hz); GC-MS: m/z=540.2557 [M]$^+$. The compound obtained was confirmed to be Compound (I-3-1).

Example 5

Synthesis of a liquid crystal compound (Compound I-3-2):

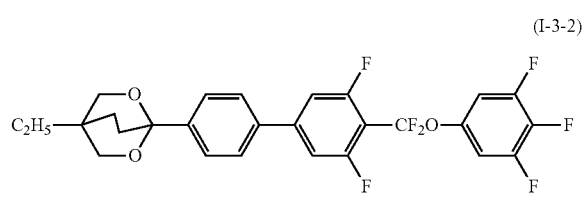

Compound (I-3-2) was synthesized according to the procedures described in [Synthesis Example 1], [Synthesis Example 2], and [Example 1], except that, for synthesizing Compound (I-3-2), [4-[difluoro(3,4,5-trifluorophenoxy)methyl]-3,5-difluorophenyl]boronic acid (0.14 mmol) was used to replace 3,4,5-trifluorophenylboronic acid used in step (b-3). The spectrum analysis for the compound obtained by the above procedures is: $^1$H-NMR (CDCl$_3$, 400 MHz), δ (ppm): 0.869(t, 3H, J=8 Hz), 0.126 (q, 2H, J=8 Hz), 1.811-1.852 (m, 2H), 2.199-2.333 (m, 2H), 4.018 (s, 4H), 6.980 (d, 2H, J=8.4 Hz), 7.203 (d, 2H, J=10.8 Hz), 7.532 (d, 2H, J=8.8 Hz), 7.630 (d, 2H, J=8.4 Hz); GC-MS: m/z=526.4153 [M]$^+$. The compound obtained was confirmed to be Compound (I-3-2).

Example 6

Synthesis of a liquid crystal compound (Compound I-4-1):

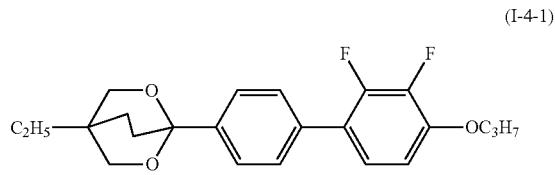

Compound I-4-1 was synthesized according to the procedures described in [Synthesis Example 1], [Synthesis Example 2], and [Example 1], except that, for synthesizing Compound (I-4-1), 4-propoxy-2,3-fluorophenylboronic acid (0.14 mmol) was used to replace 3,4,5-trifluorophenylboronic acid used in step (b-3). The spectrum analysis for the compound obtained by the above procedures is: $^1$H-NMR (CDCl$_3$, 400 MHz), δ (ppm): 0.864 (t, 3H, J=8 Hz), 1.233-1.308 (m, 5H), 1.472 (t, 2H, J=6.8 Hz), 1.804-1.844 (m, 2H), 2.199-2.278 (m, 2H), 3.991 (s,4H), 4.147 (q, 2H, J=6.8 Hz), 6.776 (td, 1H, J=8.8, 1.6 Hz), 7.069 (td, 1H, J=8.1, 2.4 Hz), 7.468 (d, 2H, J=8.4 Hz), 7.578 (d, 2H, J=8.8 Hz); GC-MS: m/z=373.9283 [M-CH$_3$]$^+$. The compound obtained was confirmed to be Compound (I-4-1).

Example 7

Synthesis of a liquid crystal compound (Compound I-1-4) of formula (I-1-4) according to the following scheme:

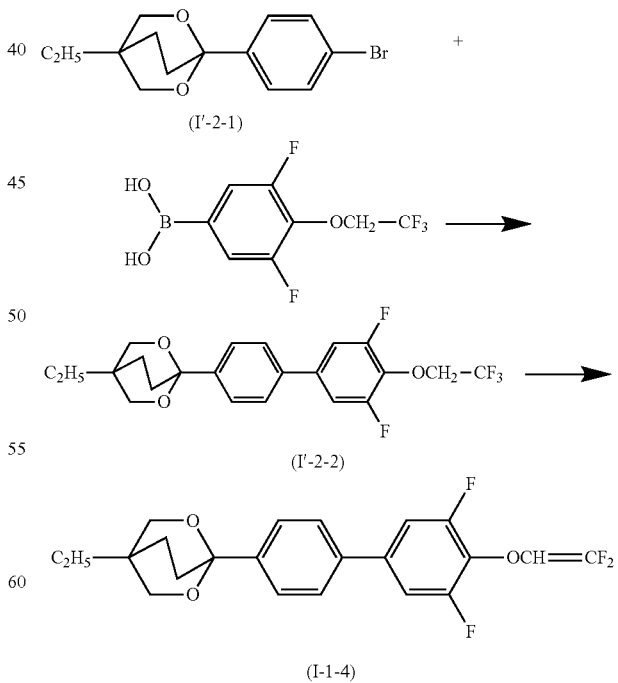

Compound I'-2-2 was synthesized according to the procedures described in [Synthesis Example 1], [Synthesis Example 2], and [Example 1], except that, for synthesizing Compound I'-2-2, 4-(2,2,2-trifluoroethoxy)-3,5-fluorophenylboronic acid (0.14 mmol) was used to replace 3,4,5-trifluorophenylboronic acid used in step (b-3). In a 100 ml three-necked bottle, diisopropylamine (0.93 g, 6.6 mmol) and 10 ml of THF were added. Then, the temperature was cooling to −10° C.~0° C., and 2.4 ml of n-butyllithium (6 mmol) was added dropwise to the three-necked bottle with stirring under nitrogen atmosphere. Thereafter, the contents in the three-necked bottle were kept at −10° C.~0° C. and continuously stirred for 1 hour for reaction to obtain a lithium diisopropylamide (LDA). To a second 100 ml three-necked bottle, compound (I'-2-2) (0.42 g, 1 mmol) and 5 ml of THF were added. Then, the temperature was reduced to −70° C.~−80° C., and the LDA reagent was added dropwise to the second three-necked bottle with stirring under nitrogen atmosphere. Thereafter, the contents in the second three-necked bottle were kept at −70° C.~−80° C. and continuously stirred for 2 hours for reaction. A thin-layer chromatography (TLC) plate (volume ratio of ethyl acetate:n-hexane=1:10) was used to check if the reaction was completed. After the reaction was completed, ml of deionized water was added to the second three-necked bottle to quench the reaction. The contents in the second three-necked bottle were extracted three times with ethyl acetate and the organic layer was collected. The organic layer was dehydrated using magnesium sulfate anhydrous and was filtered to collect a filtrate. The filtrate was condensed under a reduced pressure, followed by column chromatography (volume ratio of ethyl acetate:n-hexane=1:10) to obtain white solids (0.3 g). The spectrum analysis for the white solids is: $^1$H-NMR (CDCl$_3$, 400 MHz), δ (ppm): 0.866 (t, 3H, J=7.6 Hz), 1.282 (q, 2H, J=8 Hz), 1.806-1.846 (m, 2H), 2.219-2.260 (m, 2H), 3.992 (s,4H), 6.248-6.292 (m, 1H), 7.098-7.179 (m, 2H), 7.465 (d, 2H, J=8.4 Hz), 7.595 (d, 2H, J=8.8 Hz); GC-MS: m/z=408.3801 [M]$^+$. The white solids were confirmed to be Compound (I-1-4).

Comparative Example 1 (CE 1)

Synthesis of a liquid crystal compound of formula (CE-1) (Compound CE-1):

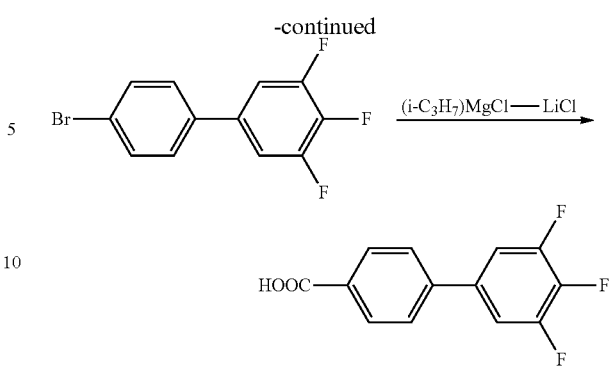

(CE-1)

Compound CE-1 was synthesized by steps (c-1) to (c-3).
In step (c-1), 3',4',5'-trifluoro-[1,1'-biphenyl]-4-carboxylic acid was synthesized according to the following scheme:

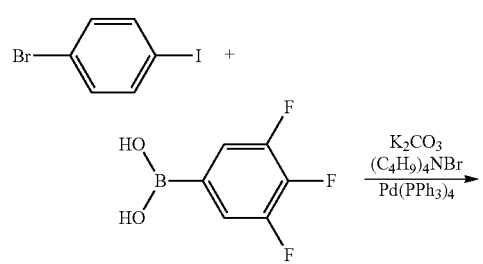

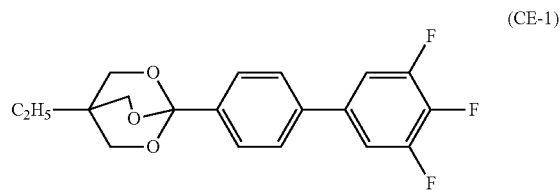

In step (c -2), 3',4',5'-trifluoro-[1,1'-biphenyl]-4-carboxylic acid (10.0 g, 37.0 mmol), 3-ethyl-3-hydroxymethyloxetane (5.9 g, 37 mmol), 4-dimethylaminopyridine (4.5 g, 37 mmol), and 100 ml of dichloromethane were mixed under nitrogen atmosphere and cooled to 0° C., and then 50 ml of a dichloromethane solution including 8.0 g (39 mmol) of dicyclohexylcarbodiimide was added dropwise thereto at 0° C., and the resulting mixture was stirred at room temperature for 15 hours. The mixture was filtrated by celite to collect a filtrate. The filtrate was condensed under a reduced pressure, followed by column chromatography (volume ratio of ethyl acetate:heptane=1:4) to obtain 13.9 g of (3-ethyloxetane-3-yl)methyl 3',4',5'-trifluoro-[1,1'-biphenyl]-4-carboxylic acid.

In step (c-3), (3-ethyloxetane-3-yl)methyl 3',4',5'-trifluoro-[1,1'-biphenyl]-4-carboxylic acid (13.9 g, 33.9 mmol) and 70 ml of dichloromethane were mixed under nitrogen atmosphere and cooled to −70° C., and then boron trifluoride-diethyl ether complex (1.2 g, 8.5 mmol) was added dropwise to obtain a mixture. After the temperature of the mixture returned to room temperature, the mixture was stirred for 15 hours. Then, 5.0 ml of triethylamine (37 mmol) was mixed with the mixture, followed by condensation using a rotary evaporator. Thereafter, 100 ml of diethyl ether was added to the resulting mixture. The resulting mixture was washed with a saturated sodium chloride aqueous solution, dried with magnesium sulfate anhydrous, and filtered to collect a filtrate. The filtrate was condensed under a reduced pressure to obtain a crude product. The crude product was subjected to column chromatography (eluent: dichloromethane), followed by recrystallization in heptane to obtain white solids (9.1 g). The spectrum analysis for the white solids is: $^1$H-NMR (CDCl$_3$, 400 MHz), δ (ppm): 0.879 (t, 3H, J=7.6 Hz), 1.321 (q, 2H, J=8.0 Hz), 4.106 (s, 6H), 7.128-7.165 (m, 2H), 7.455 (d, 2H, J=8.4 Hz), 7.678 (d, 2H, J=8.4 Hz). The white solids were confirmed to be Compound CE-1.

[Property Tests for Liquid Crystal Compound]

Each liquid crystal compound to be tested was subjected to a DSC test, and tests for determining a refractive index anisotropy (Δn), a rotational viscosity (γ1), and a dielectric anisotropy (Δε). For the DSC test, each liquid crystal compound to be tested was directly measured using a differential scanning calorimeter (DSC). For the tests for determining a refractive index anisotropy (Δn), a rotational viscosity (γ1), and a dielectric anisotropy (Δε), a test composition was prepared in advance. The test composition was prepared by mixing a mother liquid crystal composition with the liquid crystal compound to be tested. The mother liquid crystal composition was prepared by mixing three liquid crystal compounds (Compounds II-13-1, II-13-2, and II-13-3) in the same weight ratio, heating the mixture until a clear solution was obtained, and cooling the clear solution to room temperature. The chemical formulas of Compounds II-13-1, II-13-2, and II-13-3 are shown below:

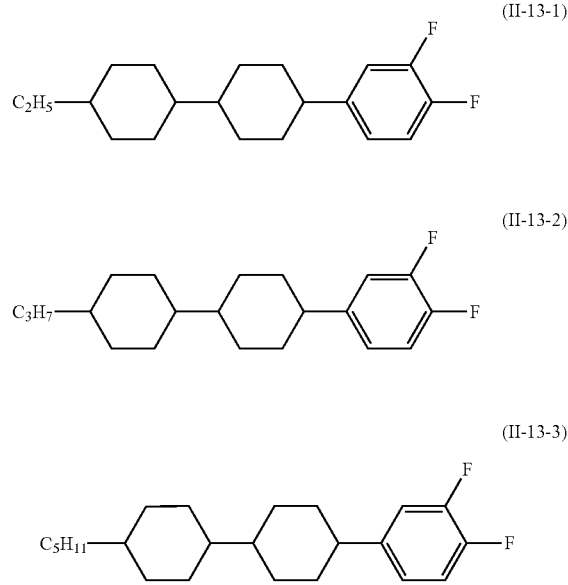

The liquid crystal compound to be tested (i.e., each of the liquid crystal compounds of Examples 1 to 7 and Comparative Example 1) was mixed with the mother liquid crystal composition to obtain the test composition. The test composition was subjected to tests to obtain the specific measured data (i.e., $\Delta n$, $\gamma 1$, and $\Delta \epsilon$). Data (i.e., $\Delta n$, $\gamma 1$, and $\Delta \epsilon$) of the mother liquid crystal composition were obtained in advance. Since the data (i.e., $\Delta n$, $\gamma 1$, and $\Delta \epsilon$) of the mother liquid crystal composition are known, the data (i.e., $\Delta n$, $\gamma 1$, and $\Delta \epsilon$) of each liquid crystal compound to be tested were calculated from the specific measured data by using extrapolation methods. The DSC test data and the calculated data for each of the liquid crystal compounds of Examples 1 to 7 and Comparative Example 1 are listed in Table 2.

DSC Test 0.5 mg to 10 mg of a liquid crystal compound to be analysed using a differential scanning calorimeter (DSC) was precisely weighed out and placed in an aluminum pan. During heating or cooling of the liquid crystal compound in the differential scanning calorimeter, phase transistions of the liquid crystal compound could be observed by the endothermic peaks or the exothermic peaks in the DSC curve. The staring points of the peaks were used to determine phase transition temperatures.

Normally, as temperature is continously raised, the phase of a liquid cyrstal compound will change from a solid crystal phase (C) to a liquid crystal phase (nematic phase, N), and then to an isotropic liquid state (I). In this test, a nematic-to-liquid transition temperature ($T_{ni}$) was observed.

Test for Determining Dielectric Anisotropy ($\Delta \epsilon$)

The test composition was fed into a liquid crystal cell. The cell was applied a voltage from 0 V to 20 V at 25° C. When the major-axis direction of the liquid crystal molecule was parallel to a base of the liquid crystal cell, a capacitance (C∥) was measured to thereby calculate a dielectric ($\epsilon$∥). When the major-axis direction of the liquid crystal molecule was perpendicular to the base of the liqud crystal cell, a capacitance (C⊥) was measured to thereby calculate a dielectric ($\epsilon$⊥) of the liquid crystal compound. A dielectric anisotropy ($\Delta \epsilon$) was calculated according to the equation $\Delta \epsilon = \epsilon \| - \epsilon \perp$.

Test for Determining Rotational Viscosity ($\gamma 1$)

The test composition was fed into a liquid crystal cell. The cell was applied a voltage of 20 V at 25° C., and a rotational viscosity ($\gamma 1$) was measured based on the dielectric anisotropy ($\Delta \epsilon$) of the test composition using an automatic liquid crystal tester (INSTEC Inc).

Test for Determining Refractive Index Anisotropy ($\Delta n$)

A surface of a main prism was rubbed in one direction, and then the test composition was dropped onto the rubbed surface of the main prism. A refractive index of the test composition was measured at 25° C. using polarized light having a wavelength of 589 nm, by means of an Abbe refractometer (ATAGO, DR-M2) with a polarizing plate mounted on an ocular lens thereof. A refractive index (n∥) was determined when the direction of the polarized light was parallel to the rubbing direction. A refractive index (n) was determined when the direction of polarized light was perpendicular to the rubbing direction. The refractive index anisotropy ($\Delta n$) of the liquid crystal compound was calculated from the equation:

$$\Delta n = n\| - n\perp.$$

TABLE 2

| Liquid crystal compound | $T_{ni}$ (° C.) | $\Delta \epsilon$ | $\gamma 1$ (mPa · S) | $\Delta n$ |
|---|---|---|---|---|
| Example 1 (Compound I-1-1) | 12.2 | 25.6 | 346.8 | 0.123 |
| Example 2 (Compound I-1-2) | 49.0 | 26.4 | 421.4 | 0.128 |
| Example 3 (Compound I-2-2) | 119 | 19.0 | 365.7 | 0.150 |
| Example 4 (Compound I-3-1) | 116 | 40.1 | 566 | 0.151 |
| Example 5 (Compound I-3-2) | 96.5 | 36.3 | 407 | 0.150 |
| Example 6 (Compound I-4-1) | 114.9 | −2.65 | 599.9 | 0.170 |
| Example 7 (Compound I-1-4) | 51.3 | 25.7 | 278 | 0.138 |
| Comparative Example 1 (Compound CE-1) | −23.1 | 36.2 | 433.5 | 0.161 |

The liquid crystal compounds of Example 1 and Comparative Example 1 have similar chemical structures, except that Compound I-1-1 of Example 1 has a dioxabicyclo[2.2.2]octane ring moiety, and Compound CE-1 of Comparative Example 1 has a trioxabicyclo[2.2.2]octane ring moiety. It can be noted from Table 2 that compared to Compound CE-1, Compound I-1-1 has a relatively high nematic-to-liquid transition temperature ($T_{ni}$), and a relatively low rotational viscosity ($\gamma 1$). In addition, Compound I-1-1 can be dissolved in a mother liquid crystal in a concentration of 10 wt %, while Compound CE-1 can be merely dissolved in a mother liquid crystal in a concentration of 2.5 wt %.

[Liquid Crystal Composition]

Liquid crystal compositions 1-10 were prepared. The amounts of the liquid crystal compounds used for preparing the liquid crystal compositions 1-10 are listed in Table 3.

TABLE 3

| | Liquid crystal composition | | | | |
|---|---|---|---|---|---|
| | 1 | 2 | 3 | 4 | 5 |
| Liquid crystal compound (I) | Compound I-1-1 (4 wt %) Compound I-3-1 (2 wt %) | Compound I-2-2 (2 wt %) | Compound I-1-2 (2 wt %) Compound I-2-1 (2 wt %) | Compound I-3-2 (3 wt %) | Compound I-1-2 (3 wt %) |
| Liquid crystal compound (II) | Compound II-1-1 (33 wt %) Compound II-2-1 (6 wt %) Compound II-3-1 (7 wt %) Compound II-6-1 (10 wt %) Compound II-11-1 (5 wt %) Compound II-13-2 (7 wt %) Compound II-13-4 (5 wt %) Compound II-16-1 (5 wt %) Compound II-6-3 (10 wt %) Compound II-13-6 (6 wt %) | Compound II-1-1 (33 wt %) Compound II-2-1 (7 wt %) Compound II-3-1 (7 wt %) Compound II-6-1 (10 wt %) Compound II-9-1 (7 wt %) Compound II-13-2 (7 wt %) Compound II-13-4 (7 wt %) Compound II-6-3 (8 wt %) Compound II-13-6 (6 wt %) Compound II-6-4 (6 wt %) | Compound II-1-1 (33 wt %) Compound II-1-3 (7 wt %) Compound II-3-1 (7 wt %) Compound II-6-1 (10 wt %) Compound II-10-2 (7 wt %) Compound II-12-1 (6 wt %) Compound II-14-1 (7 wt %) Compound II-15-1 (7 wt %) Compound II-16-2 (4 wt %) Compound II-6-3 (8 wt %) | Compound II-1-1 (33 wt %) Compound II-1-3 (7 wt %) Compound II-5-2 (7 wt %) Compound II-6-1 (10 wt %) Compound II-10-1 (7 wt %) Compound II-14-1 (7 wt %) Compound II-15-1 (12 wt %) Compound II-6-3 (10 wt %) Compound II-18-1 (4 wt %) | Compound II-1-1 (35 wt %) Compound II-1-2 (5 wt %) Compound II-3-1 (7 wt %) Compound II-6-2 (7 wt %) Compound II-10-2 (7 wt %) Compound II-12-1 (6 wt %) Compound II-14-1 (9 wt %) Compound II-15-1 (6 wt %) Compound II-17-1 (7 wt %) Compound II-13-5 (8 wt %) |

| | Liquid crystal composition | | | | |
|---|---|---|---|---|---|
| | 6 | 7 | 8 | 9 | 10 |
| Liquid crystal compound (I) | Compound I-4-1 (2 wt %) | Compound I-4-1 (2 wt %) | Compound I-1-1 (2 wt %) | Compound I-1-2 (5 wt %) Compound I-1-1 (7 wt %) Compound I-1-4 (7 wt %) | Compound I-5-1 (2 wt %) |
| Liquid crystal compound (II) | Compound II-1-1 (42 wt %) Compound II-1-3 (7 wt %) Compound II-5-1 (5 wt %) Compound II-5-3 (5 wt %) Compound II-6-1 (7 wt %) Compound II-10-1 (6 wt %) Compound II-14-1 (7 wt %) Compound II-15-1 (8 wt %) | Compound II-1-1 (55 wt %) Compound II-1-4 (7 wt %) Compound II-2-1 (7 wt %) Compound II-3-1 (8 wt %) Compound II-4-1 (7 wt %) Compound II-7-1 (5 wt %) Compound II-7-2 (6 wt %) Compound II-8-1 (3 wt %) | Compound II-1-1 (41 wt %) Compound II-1-2 (5 wt %) Compound II-3-1 (7 wt %) Compound II-6-2 (7 wt %) Compound II-10-2 (7 wt %) Compound II-12-1 (6 wt %) Compound II-14-1 (9 wt %) Compound II-15-1 (7 wt %) | Compound II-1-1 (17 wt %) Compound II-3-2 (9 wt %) Compound II-3-3 (9 wt %) Compound II-2-1 (9 wt %) Compound II-17-1 (14 wt %) Compound II-10-3 (9 wt %) Compound II-19-1 (14 wt %) | Compound II-1-1 (40 wt %) Compound II-1-3 (1.5 wt %) Compound II-16-2 (2.9 wt %) Compound II-6-3 (19.6 wt %) Compound II-2-1 (1.5 wt %) Compound II-5-3 (6.9 wt %) Compound II-5-1 (6.9 wt %) Compound II-22-1 (7.8 wt %) |

TABLE 3-continued

| Compound II-17-1 (3 wt %) | Compound II-17-1 (4 wt %) | Compound II-22-2 (7.8 wt %) |
| Compound II-6-3 (8 wt %) | Compound II-13-5 (5 wt %) | Compound II-22-3 (3 wt %) |

[Property Tests for Liquid Crystal Composition]

Each of the liquid crystal compositions 1~10 was subjected to a DSC test, and tests for determining a refractive index anisotropy ($\Delta n$), a rotational viscosity ($\gamma 1$), and a dielectric anisotropy ($\Delta \epsilon$) as described above. The liquid crystal compositions 1~10 were directly subjected to the tests. The measured data (i.e., $T_{ni}$, $\Delta n$, $\gamma 1$, and $\Delta \epsilon$) for each of the liquid crystal compositions 1~10 are listed in Table 4.

TABLE 4

| | Liquid crystal composition | | | | |
|---|---|---|---|---|---|
| | 1 | 2 | 3 | 4 | 5 |
| Tni (° C.) | 75.89 | 89.2 | 79.46 | 79.54 | 36.93 |
| $\Delta\epsilon$ | 3.01 | 2.62 | 3.95 | 4.52 | 5.07 |
| $\gamma 1$ (mPa·S) | 53.76 | 62.23 | 56.73 | 48.62 | 40.14 |
| $\Delta n$ | 0.0885 | 0.0832 | 0.0942 | 0.1102 | 0.0799 |

| | Liquid crystal composition | | | | |
|---|---|---|---|---|---|
| | 6 | 7 | 8 | 9 | 10 |
| Tni (° C.) | 74.24 | 55.42 | 56.09 | 28.61 | 72.66 |
| $\Delta\epsilon$ | 2.92 | 5.07 | 4.23 | 10.7 | 5.96 |
| $\gamma 1$ (mPa·S) | 43.25 | 40.14 | 36.73 | 61.31 | 51.62 |
| $\Delta n$ | 0.1033 | 0.0799 | 0.0793 | 0.0885 | 0.1234 |

It can be noted from Table 4 that the liquid crystal compositions, which include the liquid crystal compound (I), exhibited the general properties of conventional liquid crystal compositions. To wit, the liquid crystal compound (I) has a liquid crystal phase at a wide temperature range, good stability to heat and light, an excellent compatibility with other liquid crystal compounds, a suitable refractive index anisotropy ($\Delta n$), etc. In addition, because the liquid crystal compound (I) has a dioxabicyclo[2.2.2]octane ring moiety, it has a high dielectric anisotropy ($\Delta \epsilon$) and a low rotational viscosity ($\gamma 1$). The liquid crystal composition including the liquid crystal compound (I) may also have a wide operation temperature range, and a short response time, a lower electric consumption, a large contrast, and a low driving voltage, and thus can be used in various devices, such as liquid crystal displays, displays for personal computers, notebook computers, smart phones, etc.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A liquid crystal compound of formula (I):

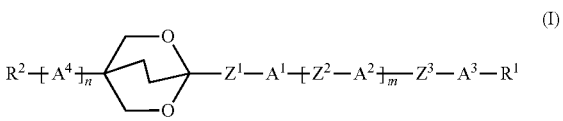

where:
$A^1$, $A^2$, $A^3$, and $A^4$ are each independently 1,4-cyclohexylene, or halogen-substituted or unsubstituted 1,4-phenylene; $R^1$ is a halogen atom, —CN, a halogen-substituted or unsubstituted C1-C10 alkyl group, a halogen-substituted or unsubstituted C2-C10 alkenyl group, a halogen-substituted or unsubstituted C2-C10 alkynyl group, a halogen-substituted or unsubstituted C1-C10 alkoxyl group, a halogen-substituted or unsubstituted C1-C10 alkylthio group, or a halogen-substituted or unsubstituted C2-C10 alkenyloxy group;

$R^2$ is a hydrogen atom, a C1-C10 alkyl group, or a halogen-substituted C1-C10 alkyl group;

$Z^1$, $Z^2$, and $Z^3$ are each independently a single bond, —COO—, —OCO—, —CF$_2$O—, —OCF$_2$—, —C≡C—, or —CH═CH—; and n and m are each independently 0 or 1.

2. The liquid crystal compound according to claim 1, wherein $A^1$, $A^2$, and $A^3$ are each independently halogen-substituted or unsubstituted 1,4-phenylene.

3. The liquid crystal compound according to claim 2, wherein $A^1$, $A^2$, and $A^3$ are each independently 1,4-phenylene, 2-fluoro-1,4-phenylene, 3-fluoro-1,4-phenylene, 2,3-difluoro-1,4-phenylene, or 3,5-difluoro-1,4-phenylene.

4. The liquid crystal compound according to claim 1, wherein $R^1$ is a halogen atom, —CN, —CF$_3$, —OCF$_3$, —OCH═CF$_2$, —OCF$_2$CF═CF$_2$, a C1-C10 alkyl group or a C1-C10 alkoxyl group.

5. The liquid crystal compound according to claim 1, wherein $R^2$ is a hydrogen atom, a C1-C5 alkyl group or a halogen-substituted C1-C5 alkyl group.

6. The liquid crystal compound according to claim 1, wherein $Z^1$, $Z^2$, and $Z^3$ are each independently a single bond or —CF$_2$O—.

7. The liquid crystal compound according to claim 1, wherein: $A^1$, $A^2$, and $A^3$ are each independently 1,4-phenylene, 2-fluoro-1,4-phenylene, 3-fluoro-1,4-phenylene, 2,3-difluoro-1,4-phenylene, or 3,5-difluoro-1,4-phenylene; $Z^1$, $Z^2$, and $Z^3$ are each independently a single bond or —CF$_2$O—; n=0; and m=0 or 1.

8. A liquid crystal composition comprises the liquid crystal compound according to claim 1.

9. The liquid crystal composition according to claim 8, further comprises a liquid crystal compound of formula (II)

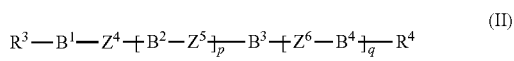

(II)

where:
- $B^1$, $B^2$, $B^3$, and $B^4$ are each independently 1,4-cyclohexylene, halogen-substituted or unsubstituted 1,4-phenylene, or 2,5-indanylene;
- $R^3$ is a hydrogen atom, a halogen atom, a halogen-substituted or unsubstituted C1-C10 alkyl group, a halogen-substituted or unsubstituted C2-C10 alkenyl group, a halogen-substituted or unsubstituted C2-C10 alkynyl group, or a halogen-substituted or unsubstituted C1-C10 alkoxyl group;
- $R^4$ is a halogen atom, —CN, a halogen-substituted or unsubstituted C1-C10 alkyl group, a halogen-substituted or unsubstituted C2-C10 alkenyl group, or a halogen-substituted or unsubstituted C1-C10 alkoxyl group;
- $Z^4$, $Z^5$, and $Z^6$ are each independently a single bond, —(CH$_2$)$_2$—, —COO—, —OCO—, —CF$_2$O—, —OCF$_2$—, —C≡C—, or —CH=CH—; and
- p and q are each independently 0 or 1.

10. The liquid crystal composition according to claim 9, wherein $R^3$ is a hydrogen atom, a C1-C10 alkyl group, and $R^4$ is a halogen atom, —CN, a C1-C10 alkyl group, a C2-C10 alkenyl group, —OCHCF$_2$, —CF$_3$, or —OCF$_3$.

11. A liquid crystal display device comprising a liquid crystal compound according to claim 1.

* * * * *